(12) United States Patent
Kazimir et al.

(10) Patent No.: US 6,287,818 B1
(45) Date of Patent: Sep. 11, 2001

(54) METHOD FOR SYNTHESIS OF N-HOMOCYSTEINE THIOLACTONYL RETINAMIDO COBALAMIN AND USES THEREOF

(75) Inventors: Michal Kazimir, Roseau (DO); F. Ray Wilson, II, Waco, TX (US)

(73) Assignee: Baylor University, Waco, TX (US)

( * ) Notice: Subject to any disclaimer, the term of this patent is extended or adjusted under 35 U.S.C. 154(b) by 0 days.

(21) Appl. No.: 09/557,664

(22) Filed: Apr. 25, 2000

(51) Int. Cl.[7] .................... C12P 19/42; C07D 231/00; C07D 333/00
(52) U.S. Cl. .................... 435/86; 548/101; 548/109; 549/3; 549/8
(58) Field of Search ................ 549/8, 3; 435/86; 548/101, 109

(56) References Cited

U.S. PATENT DOCUMENTS

| | | | |
|---|---|---|---|
| 4,255,443 | 3/1981 | McCully | 424/275 |
| 4,383,994 | 5/1983 | McCully | 424/245 |
| 4,618,685 | 10/1986 | McCully | 549/63 |
| 4,925,931 | 5/1990 | McCully | 536/25 |

OTHER PUBLICATIONS

McCully et al., "Homocysteine and lipid metabolism in atherogenesis: effect of the homocysteine thiolactonyl derivatives, thioretinaco and thioretinamide," *Atherosclerosis*, 83:197–206, 1990.

McCully et al., Homocysteine thiolactone metabolism in malignant cells, *Cancer Research*, 36:3198–3202; 1976.

McCully, "Homocysteine compounds which influence the growth of a malignant neoplasm," *Chemotherapy*, 23: 44–49; 1997.

McCully, "Antineoplastic activity of a rhodium trichloride complex of oxalyl homocysteine thilactone," *Cancer Investigation*, 5:25–30; 1987.

McCully and Vezeridis, "Antineoplastic activity of N–maleamide homocysteine thiolactone amide encapsulated within liposomes," *Proceedings of the Society of Experimental Biology and Medicine*, 180:57–61, 1985.

McCully and Vezeridis, "Chemopreventive and antineoplastic activity of N–homocysteine thiolactonyl retinamide," *Carcinogenesis*, 8:1559–1562, 1987.

McCully and Vezeridis, "Chemopreventive effect of N–homocysteine thiolactonyl retinamido cobalamin on carcinogenesis by ethyl carbamate in mice," *Proceedings of the Society for Experimental Biology and Medicine*, 191: 346–351, 1989.

McCully et al., "Inhibition of neoplastic growth by N–homocysteine thiolactonyl retinamido cobalamin," *Research Communications in Chemical Pathology and Pharmacology*, 66:117–122, 1989.

McCully et al., "Effect of the synthetic homocysteine thiolactonyl derivatives, thioretinaco, thioretinamide and thioco on growth and lactate production by malignant cells," *Research Communications in Chemical Pathology and Pharmacology*, 77:125–128, 1992.

Moon and Itri, "Chapter 14: Retinoids and cancer", In: Sporn, M.B., Roberts, A.B., Goodman, D.S. (eds), The retinoids, Academic Press, Orlando, FL., 327–371; 1984.

Kiso and Yajima, "Chapter 2: Amide formation, deprotection and disulfide formation in peptide synthesis," In: Peptides : synthesis, structures, and applications, edited by Bernd Butte, Academic Press, Inc., San Diego, CA, pp 39–53, 1995.

Spindle and McCully, "Conversion of methionine to homocysteine thiolactone in liver," *Biochimica et Biophysica Acta*, 343:687–691, 1974.

Sundaresen, "Vitamin A and the sulfate–activating enzymes," *Biochimica et Biophysica Acta*, 113:95–109, 1966.

Primary Examiner—Deborah C. Lambkin
(74) Attorney, Agent, or Firm—Fulbright&Jaworski LLP

(57) ABSTRACT

The present invention describes methods for the synthesis of N-homocysteine thiolactonyl retinamido cobalamin (thioretinaco), a compound that has potential anticancer, antineoplastic, antiviral, and antiatherogenic properties.

25 Claims, 9 Drawing Sheets

METHOD FOR SYNTHESIS OF N-HOMOCYSTEINE THIOLACTONYL RETINAMIDO COBALAMIN AND USES THEREOF

BACKGROUND OF THE INVENTION

1. Field of the Invention

The present invention relates generally to the fields of organic synthesis of bioactive compounds. More particularly, it concerns methods of synthesis for N-homocysteine thiolactonyl retinamido cobalamin ("thioretinaco"), a compound that has potential antineoplastic, anticarcinogenic, antiatherogenic, chemopreventive, antiviral, and antiaging activities.

N-homocysteine thiolactonyl retinamido ("thioretinamide") is a starter material for the preparation of thioretinaco.

2. Description of Related Art

McCully (U.S. Pat. No. 4,618,685; "the '685 patent", incorporated herein by reference) attempted to synthesize thioretinamide, the precursor to the compound of the invention, from homocysteine thiolactone free base and retinoic acid. McCully's synthesis of thioretinamide involves the conjugation of homocysteine thiolactone to retinoic acid using dicyclohexylcarbodimide as a coupling agent. The process in that patent starts with the preparation of the free base of homocysteine thiolactone. This is done by dissolving sodium hydroxide (NaOH) in water, adding methylene chloride and rapidly mixing. Homocysteine thiolactone hydrochloride is then slowly added to the mixture. After 15 minutes of mixing, the methylene chloride layer is separated, dried over anhydrous sodium sulfate and the solvent is evaporated under reduced pressure at 37° C. The resulting clear liquid (homocysteine thiolactone free base) is immediately added to tetrahydrofuran (or any other non-polar solvent) containing all-trans-retinoic acid. Then, dicyclohexylcarbodiimide is added, and the reaction mixture is stirred 16 hours at 20° C., protected from light. The tetrahydrofuran is removed at 37° C. under reduced pressure, and the yellow-white residue is added to 500 ml of water and 500 ml of ethyl acetate. The mixture is stirred vigorously for one hour, and the ethyl acetate layer is separated and dried over anhydrous sodium sulfate. The ethyl acetate is concentrated to about 20 ml at 50° C. under reduced pressure and cooled. The resulting N-homocysteine thiolactonyl retinamide, (a yellow powder) was produced with a 69% theoretical yield and a melting point of 172° C.

Unfortunately, it has recently been shown that the method described in the '685 patent does not produce thioretinamide in pure form. The inventors of the present invention attempted the method of the '685 patent, as described in McCully and Vezeridis, 1987a, and were unsuccessful in obtaining sufficient, pure thioretinamide as confirmed by subsequent analysis by 300 MHz N.M.R. Proton N.M.R. analysis of the compounds produced by McCully's method did not give conclusive evidence that the compound produced was thioretinamide. When the present inventors attempted to repeat the method described in the '685 patent, they conclusively showed that a major product of this procedure was the byproduct dicyclohexylurea (DCU). In sum, the procedure described in the above-listed references did not produce thioretinamide in the expected quantity or purity. Therefore, this procedure did not provide an efficient basis for producing thioretinamide for use in the preparation of thioretinaco.

Despite the difficulties in synthesizing thioretinamide following the procedures described in the '685 patent, the work of McCully showed that there was promise for thioretinamide as a therapeutic. The "thioretinamide" synthesized as described was able to counteract the carcinogenecity of ethyl carbamate in pulmonary neoplasms of strain A female mice. Thioretinamide decreased the number of tumors formed to 80% at doses of 50 mg/week, and 60% at doses of 200 mg/week. Unfortunately, the mice receiving the higher dose showed significant weight loss (McCully and Vezeridis, 1987a).

In U.S. Pat. No. 4,925,931 ("the '931 patent"; incorporated herein by reference), thioretinamide has been shown to react with cobalamin to form N-homocysteine thiolactonyl retinamido cobalamin, also known as thioretinaco. Both thioretinamide and thioretinaco have anticarcinogenic and antineoplastic activities. (McCully and Vezeridis, 1987a; McCully and Vezeridis, 1989). In experiments with cultured malignant and normal cells, thioretinaco was found to have antiproliferative activity, and thioco, the complex of homocysteine thiolactone and cobalamin, was found to increase growth of both malignant and normal cells. (McCully et al., 1992). Intratumoral administration of thioretinaco decreased the growth of human pancreatic adenocarcinomas in athymic mice. (McCully et al., 1989).

The above-described studies and patents pointed to great promise for thioretinamide and thioretinaco as chemotherapeutic agents. However, in order to fully realize the potential of this agent, methods of producing them in sufficient quantities and purity are needed. Co-pending U.S. Pat. No. 6,054,595, filed Jun. 29, 1999, and issued Apr. 25, 2000, incorporated herein by reference in its entirety, describes the development of methods that produces high yields of pure N-homocysteine thiolactonyl retinamide (thioretinamide).

SUMMARY OF THE INVENTION

The present invention presents efficient, high-yield methods for the synthesis of N-homocysteine thiolactonyl retinamido cobalamin (thioretinaco). The compound produced using the methods of the invention is more pure than that obtained using previously taught methods, thereby overcoming deficiencies existing in the art. Thioretinaco is useful for chemoprevention and chemotherapy of malignant neoplasms in animals and as an anti-atherogenic agent. The thioretinaco produced using the methods of the invention, overcome the disadvantage of toxicity of chemotherapeutic compounds and retinoids, because they are composed of retinoic acid, homocysteine thiolactone, and/or cobalamin (i.e. co-enzyme B12), bound together in a non-toxic form. Both compounds can be given in large doses without toxicity.

The method for producing thioretinaco of the present invention utilizes N-homocysteine thiolactonyl retinamide produced by the methods described in co-pending U.S. patent application Ser. No. 09/340,496 filed Jun. 29, 1999 incorporated herein by reference ("the '496 application"). The '496 application describes methods that produce high yields of substantially pure N-homocysteine thiolactonyl retinamide. The phrase "substantially pure" means that the compound produced by the methods of the invention will have a purity of greater than about 70% and will be substantially free of by-products and intermediates that may be produced in the reaction. As stated above, the compounds of the invention are superior to previously produced compounds in that the purity and yield is higher than what has previously been obtained.

The method described in the '496 application is unique in that the reaction is performed in a single container.

Homocysteine thiolactone is prepared "in situ" and a retinoic acid moiety is added directly to the same reaction mixture to obtain homocysteine thiolactionly retinamide, making the procedure more efficient. The synthesized product is then analyzed for purity and yield by using 300MHz N.M.R. and mass spectroscopy.

The novel synthesis of thioretinamide comprises conjugating retinoic acid with a homocysteine thiolactone using one or more coupling agents. Preferably, two coupling agents are used for the synthesis of thioretinamide. The starting material for the reaction can be homocysteine thiolactone in racemic form (DL-homocysteine thiolactone hydrochloride), or in the form of L-homocysteine thiolactone hydrochloride, D-homocysteine thiolactone hydrochloride or homocysteine thiolactone hydrochloride free base.

The preferred coupling agent used to conjugate the retinoic acid with the homocysteine thiolactone in making thioretinamide is N-ethyl-N'(3-dimethyl-aminopropyl) carbodiimide. A second coupling agent, such as 1-hydroxybenzotriazole; 3-hydroxy-4-oxo-3, 4-dihydro-1,2,3-benzotriazine; or benzotriazole-1-methyloxytris(dimethylamino)phosphonium hexafluorophosphate, may be used in the reaction. Furthermore the reaction is performed preferably under conditions of reduced light and under an atmosphere of argon.

The thioretinamide and thioretinaco compounds produced by the methods of the present invention may be analyzed by nuclear magnetic resonance spectroscopy and mass spectroscopy. The molecular weight of the thioretinamide synthesized by the methods of the invention was found to be about 399 by mass spectroscopy analysis and the melting point was in the range of 150° C.–170° C. Preferably, the melting point of the thioretinamide produced by the methods of the present invention will be about 155° C.–165° C. and even more preferably, about 157° C.–159° C. It will be understood by one of skill in the art that the melting point can be any of the values in the described ranges; that is about 150° C., 151° C., 152° C., 153° C., 154° C., 155° C., 156° C., 157° C., 158° C., 159° C., 160° C., 161° C., 162° C., 163° C., 164° C., 165° C., 166° C., 167° C., 168° C., 169° C., and/or 170° C., including values between each degree, such as 190.1° C., 190.2° C., etc.

Significantly, the yield of thioretinamide produced by the methods of the present invention is greater than 70% of a calculated theoretical yield. It will be understood that the yield can be greater than or equal to 70% for example, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, including all decimal values between percentages, of a calculated theoretical yield.

It is envisioned that any solvent may be used to dissolve the retinoic acid used in the synthesis of thioretinamide. Preferred solvents include $N_1N$-dimethylformamide and ethyl acetate.

An alternate method for the synthesis of thioretinamide utilizes homocysteine thiolactone hydrochloride as the starting material. In that method, homocysteine thiolactone hydrochloride is conjugated with retinoic acid using two coupling agents. By "conjugated" it is meant that a covalent bond is formed between the primary amine of homocysteine thiolactone and the carboxy group of retinoic acid such that a substituted amide is produced. The homocysteine thiolactone can be racemic (DL-homocysteine thiolactone hydrochloride), L-homocysteine thiolactone hydrochloride or D-homocysteine thiolactone hydrochloride. The conjugation comprises using N-ethyl-N'-(3-demethyl-aminopropyl) carbodiimide and a second coupling agent. The second coupling agent may be 1-hydroxybenzotriazole; 3-hydroxy-4-oxo-3, 4-dihydro-1,2,3-benzotriazine; or benzotriazole-1-methyloxytris(dimethylamino)phosphonium hexafluorophosphate.

The method for synthesizing thioretinamide may preferably use DL-homocysteine thiolactone hydrochloride as the starting material. This racemic homocysteine thiolactone hydrochloride is conjugated retinoic acid using N-ethyl-N'-(3-demethyl-aminopropyl)carbodiimide and a second coupling agent. The second agent may be chosen from 1-hydroxybenzotriazole; 3-hydroxy-4-oxo-3, 4-dihydro-1,2, 3-benzotriazine; or benzotriazole-1-methyloxytris (dimethylamino) phosphonium hexafluorophosphate.

In another preferred embodiment, N-ethyl-N'-(3-dimethylaminopropyl) carbodiimide (EDC) and 1-hydroxybenzotriazole (HOBt) may be used as coupling agents. The final product is isolated by an aqueous wash using several aqueous solutions to separate out by-products and produce substantially pure thioretinamide in solution.

The homocysteine thiolactonyl retinamide synthesized by the methods described in the '496 patent is substantially pure and can be used to synthesize substantially pure thioretinaco at high yields.

In one embodiment the invention describes, a method for the synthesis of N-homocysteine thiolactonyl retinamido cobalamin comprising, conjugating thioretinamide with 5'-deoxyadenosine cobalamin for use in preparing the thioretinaco of the present invention, the thioretinamide may be racemic (DL-N-homocysteine thiolactonyl retinamide) or L-N-homocysteine thiolactonyl retinamide or D-N-homocysteine thiolactonyl retinamide. The thioretinamide used to prepare the thioretinaco of the present invention is prepared by the methods described above and in the '496 application.

It is recognized that some authors spell cobalamin with an "e" on the end, i.e., "cobalamine." It would be understood by one of skill in the art that these are references to the same compound.

In another aspect of the method of the invention, the 5'-deoxyadenosine cobalamin includes any isomeric variant or other variations. Isomers, stereoisomers, or variations of B12 (cobalamin) may include forms where the substituent of the cobalt atom that is normally attached to the 5'-deoxyadenosyl unit is attached to a methyl group ($-CH_3$) or a hydroxy group ($-OH$). When the hydroxy group is attached to the cobalt atom, it is in the +3 oxidation state. There is a dimethylbenzimidazole component attached to the cobalamin opposite to where the 5'-deoxyadenosyl unit attaches.

In further embodiments, the method can also comprise the use of at least one conjugating agent. It is contemplated that any known conjugating agents would be useful in the method of the invention.

In another embodiment, the reaction is performed under conditions of reduced light and under an atmosphere of argon.

In other embodiments the method further comprises analysis of the product by nuclear magnetic resonance spectroscopy, X-ray crystallography and/or mass spectroscopy.

In a specific aspect of the invention the solvent used to dissolve N-homocysteine thiolactonyl retinamide is ethanol. The method can further comprise evaporating the ethanol under reduced pressure.

In another specific aspect, the solvent used to dissolve the mixture of the N-homocysteine thiolactonyl retinamide and the 5'-deoxyadenosine cobalamin retinoic acid is hydrochloric acid.

Alternative solvents envisioned for use in the present invention include any non-polar/organic solvents, e.g., chloroform, acetone, benzene, hexane, methanol, etc. The same conditions apply for thioretinaco as do for the synthesis of thioretinamide as listed under "solvents of reaction."

As used in the specification and claims the words "a" and "an" when used in combination with the conjunction "comprising" denote "one or more than one".

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

The graph shows 27 peaks that correspond to 24 carbon atoms of thioretinamide and 3 carbon atoms, at approximately 77 ppm, that correspond to the solvent chloroform.

Figure 9:
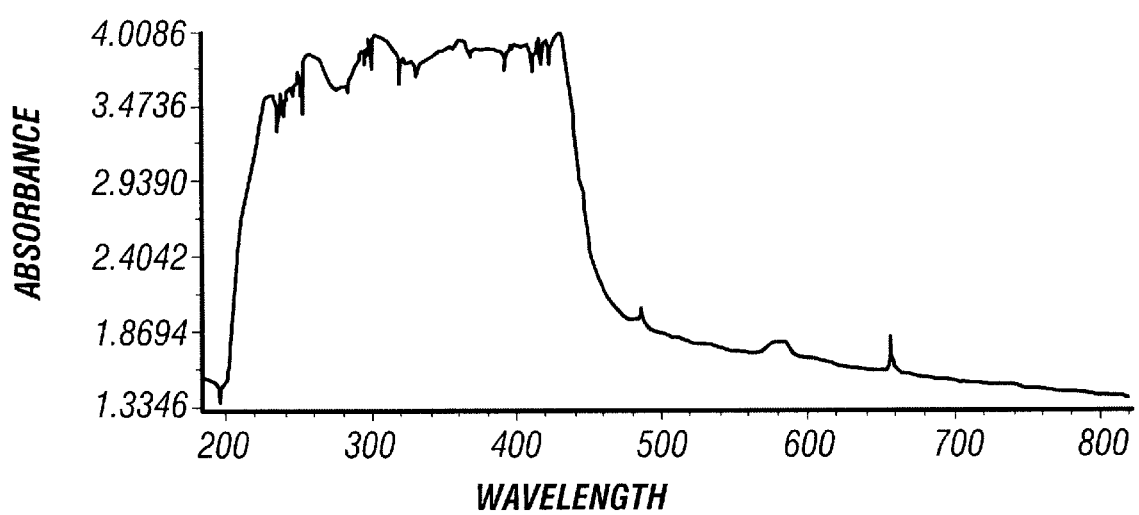

FIG. 9. U.V.-Visible Spectroscopy of Thioretinamide made according to the invention.

DESCRIPTION OF ILLUSTRATIVE EMBODIMENTS

A. The Present Invention

The compound produced by the methods of this invention is N-homocysteine thiolactonyl retinamido cobalarnin and may be abbreviated to thioretinaco. Thioretinaco has potential antineoplastic, antiaging, antiviral and antiatherogenic properties.

Thioretinaco is produced herein by conjugating thioretinamide with 5'-deoxyadenosine cobalamin (also referred to as co-enzyme B12). The reaction is carried out under conditions of reduced light and under an atmosphere of argon by using ethanol to dissolve thioretinamide. The co-enzyme B12 is added and mixed by warming at 37° C. to create a burgundy-tan colored solution. The two components are conjugated by the slow addition of hydrochloric acid with a microcapillary tube until complete dissolution occurred in the mixture. The solution is then stirred at 37° C. for 6 to 12 hours and the ethanol is subsequently evaporated off at 37° C. under reduced pressure until a crimson orange powder of thioretinaco is obtained.

Figure 1:
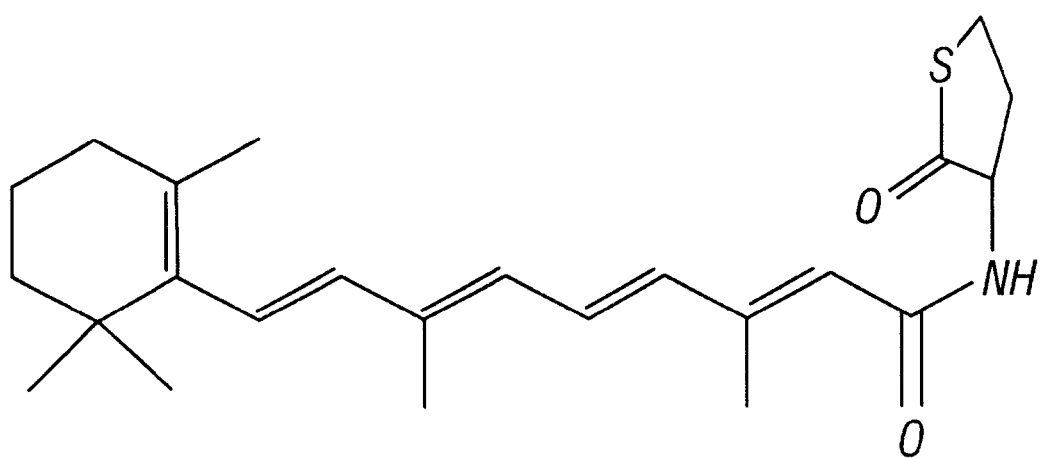
FIG. 1. Structure of homocysteine thiolactonyl retinamide (thioretinamide).
Figure 2:
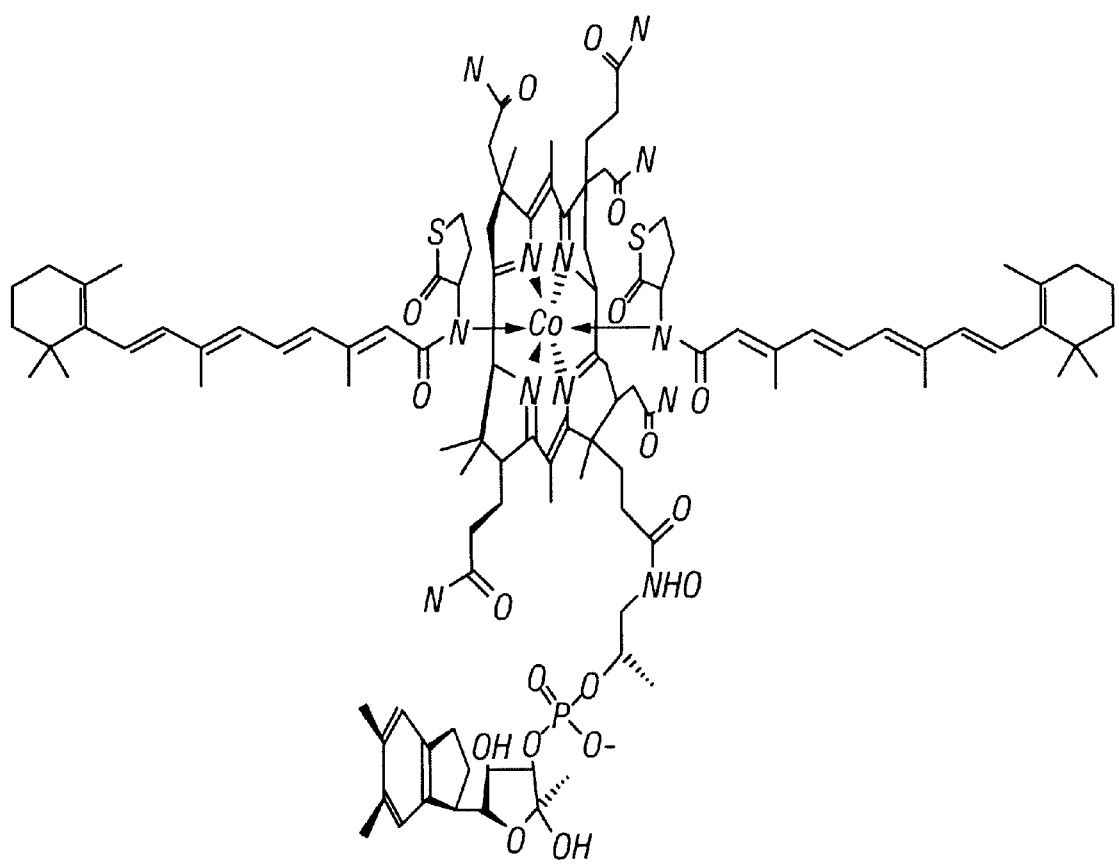
FIG. 2. Structure of N-homocysteine thiolactonyl retinamido cobalamin (thioretinaco).

One of the methods of this invention describe the synthesis of thioretinaco using N-homocysteine thiolactonyl retinamide prepared by the methods described in co-pending U.S. patent application Ser. No. 09/340,496. The structure of the thioretinamide is shown in FIG. 1 and the structure of thioretinaco is depicted in FIG. 2.

The method described herein for producing thioretinaco is superior to previously known methods in that it produces thioretinaco in higher yields with higher purity. The resulting compounds may be used in cancer chemotherapy and chemoprevention with lower toxicity than other known chemotherapeutic compounds. The reduced toxicity of the compounds of the invention results from their components, retinoic acid, homocysteine thiolactone and/or cobalamin, being bound together in a non-toxic form.

B. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Synthesis of Homocysteine Thiolactonyl Retinamido Cobalamin (Thioretinaco)

Thioretinaco consists of two molecules of an N-substituted derivative of homocysteine thiolactone which are conjugated to two unsaturated, trans forms of retinoic acid or retinamide. These two thioretinamide molecules are conjugated to either side of the cobalamin molecule of 5'-deoxyadenosine cobalamin and are depicted in FIG. 2.

In one embodiment of this method, the synthesis of thioretinaco may utilize N-homocysteine thiolactonyl retinamide (thioretinamide), as synthesized by the methods outlined in the Examples below and also described by Kazimir and Wilson in U.S. patent application Ser. No. 09/340,496 filed Jun. 29, 1999. However, as will be appreciated by one of skill in the art, variants of this method and other methods whereby thioretinamide is synthesized may be used as well.

The procedure was performed by the inventors under conditions of reduced light and under an atmosphere of argon according to the following steps:

Step 1: 0.025 mmol (10 mg) of thioretinamide was dissolved in 100 ml of ethanol at 37° C.

Step 2: To the dissolved yellow solution, 0.050 mmol (20 mg)of 5'-deoxyadenosine cobalamin (coenzyme B12) was added. This was followed by mixing and warming at 37° C. which created a burgundy-tan colored solution.

Step 3: Up to 5 μl of 12M hydrochloric acid was slowly added to the solution using a microcapillary tube until complete dissolution occurred in the mixture. At this point the solution attains a slight orange tinge.

Step 4: The solution was stirred at 37° C. for 6 to 12 hours. Subsequent evaporation of the ethanol at 37° C. under reduced pressure yields a crimson orange powder.

Alternative methods of thioretinaco synthesis are also envisioned to be within the scope of the present invention. These methods include the addition of an agent which would aid in conjugation of the thioretinamide to the cobalamin molecule of coenzyme B12. It is contemplated that any known conjugating agents would be useful in the method of the invention.

Although the use of ethanol as a solvent is described in the method the inventors contemplate the use of other solvents, known to one of skill in the art, for the synthesis of thioretinamide. Alternative solvents envisioned for use in the present invention include any non-polar/organic solvents, e.g., chloroform, acetone, benzene, hexane, methanol, etc. The same conditions apply for thioretinaco as do for the synthesis of thioretinamide as listed under "solvents of reaction."

Furthermore, the use of isomeric variant forms and other variations of coenzyme B12 and/or thioretinamide are also contemplated. These forms may be with or without post-conjugational modifications. Post-conjugational modifications may include addition or removal of groups/moieties which may or may not have a functional purpose (e.g., methyl group addition or removal, cis/trans bond transformation).

Analysis of thioretinaco

Figure 3:
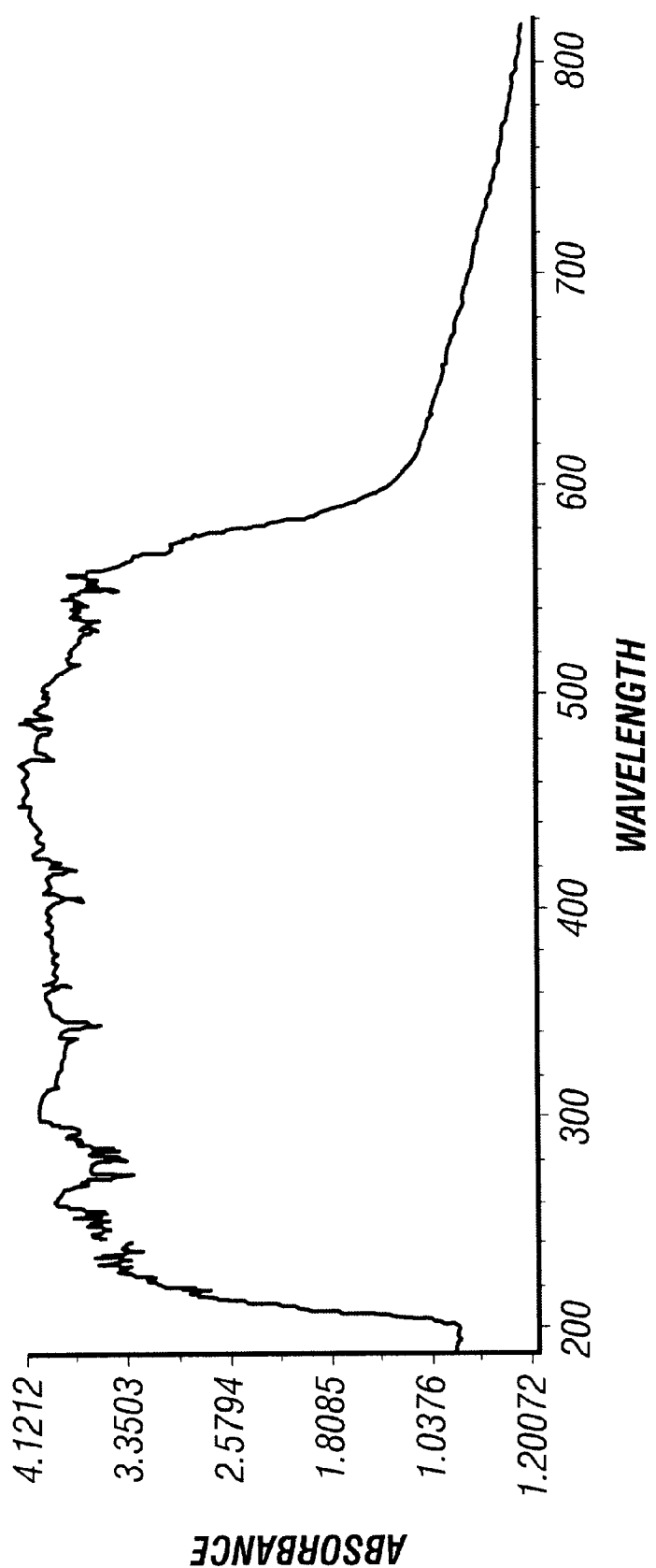
FIG. 3. U.V.-Visible Spectroscopy of N-homocysteine thiolactonyl retinamido cobalamin (thioretinaco) made according to the invention.
Figure 4:
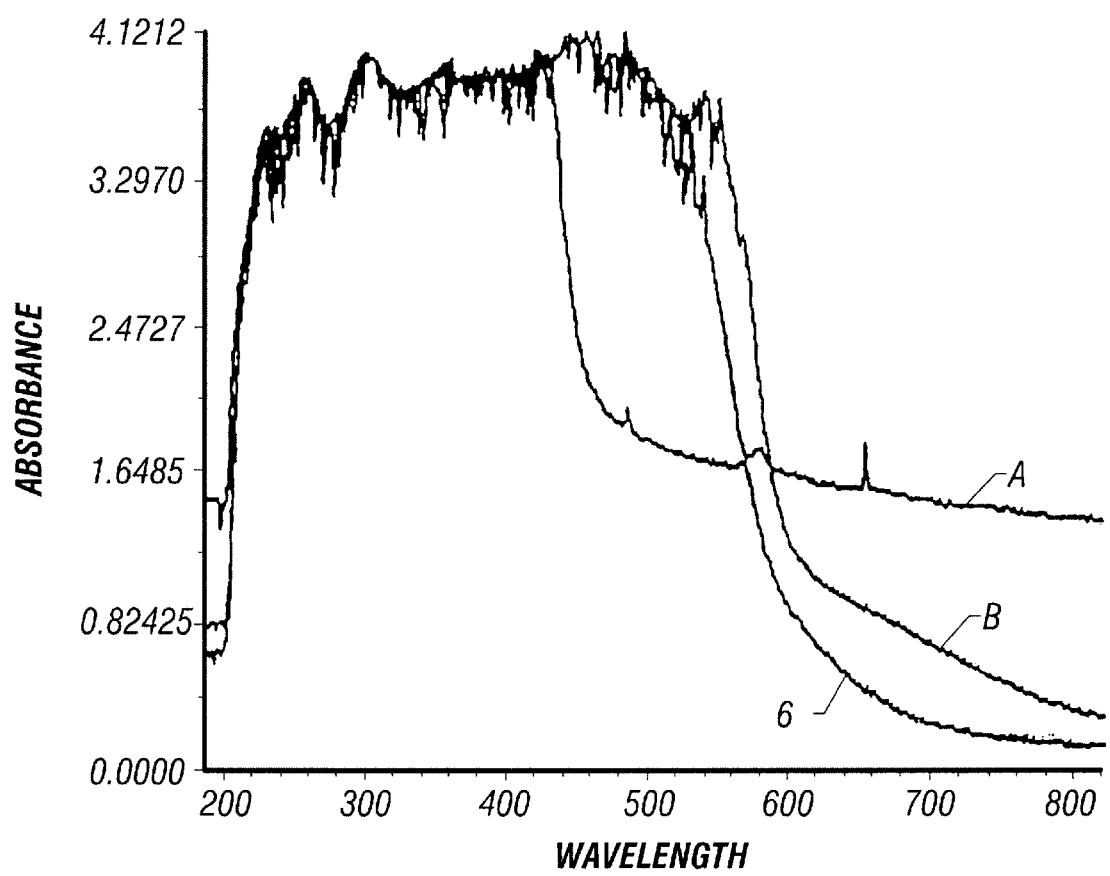
FIG. 4. U.V.-Visible Spectroscopy of A. thioretinamide; B. thioretinaco (thoiretinamide +co-enzyme B-12); and C. Coenzyme B-12.

To analyze the thioretinaco synthesized the inventors performed UV/visible spectrophotometry. For this the samples were dissolved in propylene glycol at equimolar concentrations of 3.15 mmol/ml and balanced to pH 2 with 1M sodium hydroxide and 1 M hydrochloric acid. Ultraviolet (UV) and visible absorbence spectra (at 200 nm to 800 nm) of thioretinaco was determined using a Beckman DU-640 spectrophotometer (FIG. 3). Absorption spectra (at 200 nm to 800 nm) were determined for constituents thioretinamide and coenzyme B12 and compared to thioretinaco (FIG. 4).

It is also noted that x-ray crystallography is an acceptable way to analyze thioretinaco.

EXAMPLE 2

Synthesis of N-Homocysteine Thiolactonyl Retinamide

The compound produced by methods described in this invention, thioretinaco, is produced from N-homocysteine thiolactonyl retinamide (thioretinamide). This example describes the synthesis of thioretinamide as set forth in co-pending U.S. Pat. No. 6,054,595 incorporated herein by reference. Thioretinamide is an N-substituted derivative of homocysteine thiolactone which is conjugated to retinoic acid or retinamide. The steps involved in the synthesis of thioretinamide are as outlined below. However, for the purposes of this invention thioretinamide may be synthesized by alternative methods as well, some of which are described in Example 3, and one of skill in the art will appreciate that the invention is not limited to the synthesis described below.

Under conditions of reduced light and an atmosphere of argon, all-trans-retinoic acid, 0.666M (0.200 grams) (Sigma Chemical Co., Missouri), is dissolved in 20 ml of argon protected anhydrous tetrahydrofuran (THF). After stirring ten minutes, the transparent yellow solution is placed in an ice water bath and stirred while the temperature was decreased to 0° C. After stirring at 0° C. for 30 minutes, 1.0 mM (0.1912 grams) of N-ethyl-N'-(3-dimethylaminopropyl) carbodiimide (EDC) (Sigma Chemical Co., St. Louis, Mo.) is added, followed immediately by one mM (0.1350 grams) of 1-hydroxybenzotriazole (HOBt) (Sigma Chemical Co., Missouri). The solution is removed from the ice water bath and heated to 40° C. using oil bath and stirred for three to four hours. (In some preparations, N,N-dimethylformamide (DMF) (Sigma Chemical Co., Missouri) is added drop-wise in order to dissolve all of the EDC and HOBt, but this makes it difficult to separated the final compound from DMF in later steps and yield is compromised.) Two mM of diisopropylethylamine (DIEA) (Sigma Chemical Co., Missouri) (0.2585 grams or 0.35 ml at d=0.7420) is added to the stirring mixture using a syringe. (The solution will be completely dissolved and transparent.) The solution temperature is reduced to 0° C. in an ice water bath and 0.666 mM (0.1026 grams) DL-homocysteine thiolactone hydrochloride is added with rapid mixing. While maintaining protection from light and under an atmosphere of argon, the solution is stirred at 0° C. for 60 minutes followed by gradual temperature increase to 24° C. and stirred for 16 to 20 hours. The solution is subjected to thin layer chromatography at hourly intervals to monitor completion of reaction. Solvent is removed at 37° C. under reduced pressure and the mixture is dried using a vacuum pump aided by a $CO_2$/acetone cooled distillation apparatus. (The resulting powder is yellow in color or an orange/brown viscous residue if DMF is used.)

The non-reacted components of the synthesis are removed using aqueous washes. The mixture is suspended in 12 ml ethyl acetate (EtOAc) (Sigma Chemical Co., St. Louis, Mo.). Aqueous washes are performed using a 50 ml separatory funnel. Separations are performed using 10 ml distilled $H_2O$ (3X), followed by 10 ml of distilled $H_2O$ saturated $NaHCO_3$ (3X), followed by 10 ml of distilled $H_2O$ saturated NaCl (3X), followed by 10 ml of 2N HCl (3X), and followed by a final wash with 10 ml of distilled $H_2O$ saturated with NaCl. The product is dissolved in the organic layer, which is positioned above the aqueous layer. The organic layer containing thioretinamide is placed in an Erlenmeyer flask and dried over excess sodium sulfate ($Na_2SO_4$) for 2 to 12 hours in the dark at 24° C.

Figure 5:
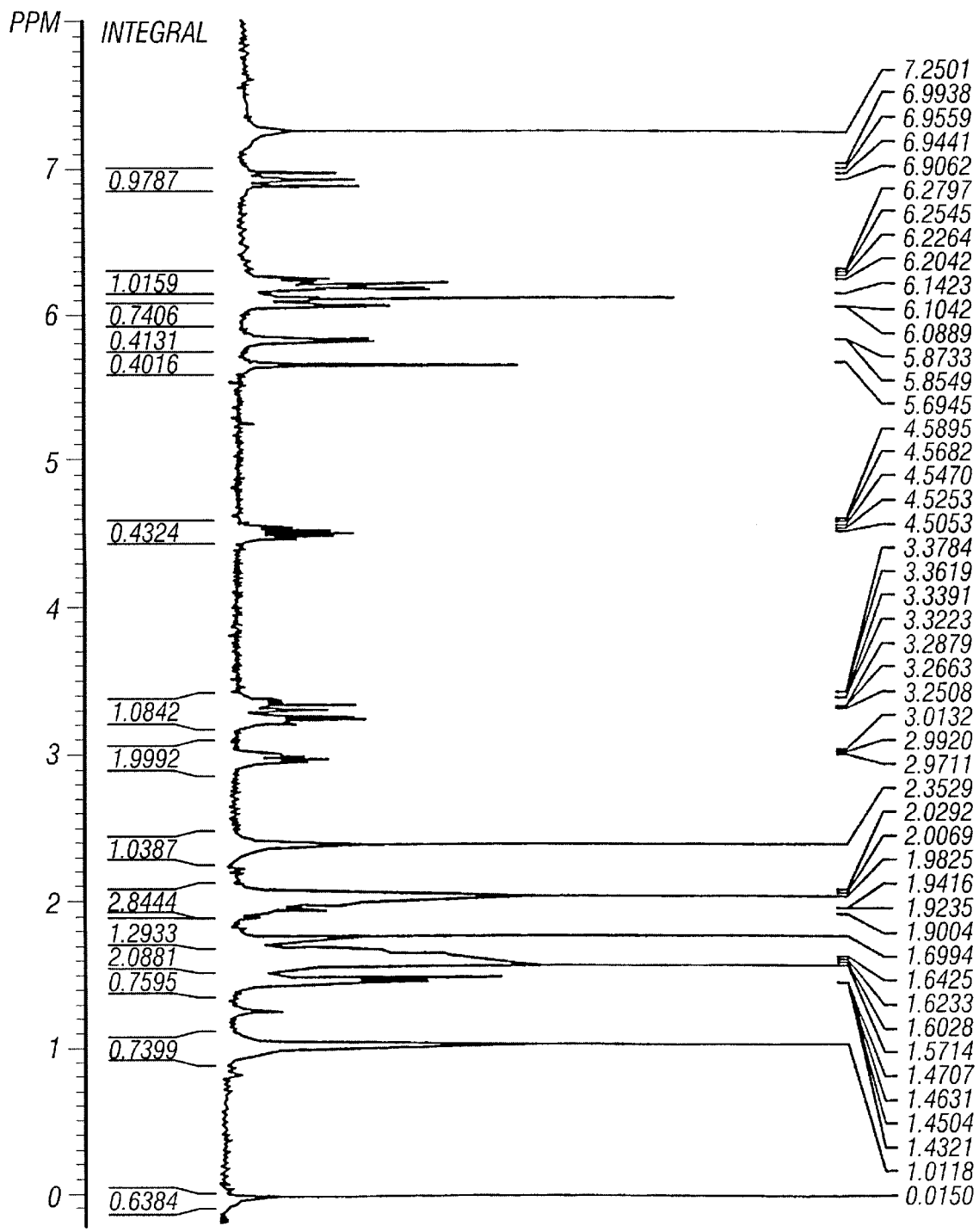
FIG. 5. Proton N.M.R. of homocysteine thiolactonyl retinamide made according to the invention. 300 mHz proton N.M.R. of thioretinamide was performed while dissolved in chloroform. N.M.R. signals of homocysteine thiolactone (FIG. 6) and retinoic acid (FIG. 7) are incorporated into the current N.M.R. Downfield shifting of proton signals of amnide hydrogen at 4.5 ppm gives evidence that the molecules are conjugated.

Thioretinamide is separated from the sodium sulfate mixture by filtration and purified by recrystalization in EtOAc. The product is in the form of a yellow crystalline powder. Thioretinamide is a yellow crystal or powder when in pure form. Characterization of thioretinamide is performed using 300 mHz nuclear magnetic resonance spectroscopy (N.M.R.). Thioretinamide is further characterized by mass spectroscopy and melting point determination. The results of the analysis of the thioretinamide produced by these methods are summarized as follows:

300 mHz proton and carbon nuclear magnetic resonance spectroscopy (N.M.R.) (FIGS. 2 and 5)

molecular weight is about 399.22 melting point is about 156–158° C.

synthesis yield is greater than 70% theoretical

The analysis is described in detail in Example 4. Alternative methods of thioretinamide synthesis would differ in respect to the agent used to conjugate or couple the homocysteine thiolactone to the retinoic acid. It is contemplated that the coupling agents may include compounds such as 1,1 -carbonyldiimidazole and isopropylcarbodiimidizole. In addition to the solvents tetrahydrofuran, N,N-dimethylformamide, and ethyl acetate used in the synthesis of thioretinamide, the inventors contemplate the use of different non-polar or organic solvents which should not alter the synthesis of thioretinamide.

Thioretinamide produced by this method has a melting point of 156–158° C. whereas the synthesis used by McCully and Vezeridis, 1987a, had a melting point of 172–173° C. Thus, the compound synthesized by this is different and has been demonstrated to be in a more pure form by N.M.R. analysis.

EXAMPLE 3

Modifications for the Synthesis of Thioretinamide

All of the compositions and/or methods described in this example can be made and executed without undue experimentation in light of the present disclosure. While the compositions and methods for the synthesis of thioretinamide have been described in terms of preferred embodiments in Example 2, it will be apparent to those of skill in the art that variations may be applied to the compositions and/or methods disclosed and in the steps or in the sequence of steps of the method described in Example 2. All such similar substitutes and modifications apparent to those skilled in the art are deemed to be within the spirit, scope and concept of the method as variations to produce thioretinamide and are presented in this Example. Thus, the following factors can be changed in the procedure described in Example 2.

Coupling Reagents

Different coupling agents, other than those described in Example 2, may be used to produce thioretinamide. The synthesis of thioretinamide involves a coupling reaction which is an amide-forming reaction between homocysteine thiolactone and retinoic acid. Appropriate activation is required to perform the coupling. Carboxyl activation is the method of choice for the present invention as opposed to amino activation. This example describes alternative activation procedures, reagents, and methods that may also be used to synthesize thioretinamide.

A. Acid Chloride and Fluoride Methods: The amide bond required for the synthesis of thioretinamide can be obtained using acid chlorides or fluorides by treating a homocysteine thiolactone and retinoic acid with either $PCl_5$, $PCl_3$, $SOCl_2$, or $(COCl)_2$.

B. Active Ester Methods: Active esters can be prepared by the dicyclohexylcarbodiimide (DCC) or mixed anhydride method from N-protected amino acids and alcohol. Transesterification methods using trifluoroacetate and trichloroacetate may also be used.

(i) Phenyl Esters: Generally, phenols which have electron-withdrawing substituent in the ortho or para position can be used as active esters. For example, 2,4,5-trichlorophenol, pentachlorophenol, and pentafluorophenol may be used. After the coupling reaction with a phenol-type active ester, the liberated acidic phenol must be removed by an appropriate method (i.e. washing with a aqueous sodium carbonate or recrystalization) as will be apparent to one of ordinary skill in the art.

(ii) N-Hydroxylamine Esters: A series of N-hydroxylamine-type esters represented by N-hydroxysuccinimide (HOSu) ester can be used. HOSu esters are prepared by coupling N-protected amino acids and HOSu by DCC. N-hydroxybenzotriazole (HOBt) esters which are also used in peptide synthesis are prepared using DCC. 3-hydroxy-4-oxo-3,4-dihydro-1,2,3-benzotriazine (HOOBt) is another alternative reagent to HOBt.

(iii) Bifunctional Active Esters: Various bifunctional active esters such as hydroxyquinoline, catechol, and hydroxypyridine may be used as racemization-free reagents for amide formation between a homocysteine thiolactone and retinoic acid.

C. Unsymmetrical Anhydride Methods:

(i) Mixed Anhydride Method: The mixed anhydride method for amide-bond formation (also used for peptide bond formation) involves aminolysis of an anhydride consisting of an N-protected amino acid and another acid. The carboxylic-carboxylic mixed anhydride method and carbonic-carboxylic mixed anhydride methods can be used. Isobutychloroformate is commonly used for the preparation of carbonic-carboxylic mixed anhydrides.

Mixed anhydrides are also obtained by the reaction of amino acids and dihydroquinoline derivatives (such as, 1-ethoxycarbonyl-2-ethoxy-1,2-dihydroquinoline (EEDQ) or 1-isobutyloxycarbonyl-2-isobutyloxy-1,2-dihydroquinoline (IIDQ)).

(ii) Phosphoric Mixed Anhydride Methods: The mixed anhydrides of amino acids and phosphoric acids are also useful for formation of the peptide bond. The phosphoric reagents that may be used include $(PhO)_2P(O)Cl$ and $Me_2P(S)Cl$. In this category, 3,3'-(chlorophosphoryl)bis(1,3-oxazolidin-2-one) (BOP-Cl) is particularly useful for coupling of imino acids because of the strong reactivity and selectivity toward the amine component. Norborn-5-ene-2,3,-dicarboximido diphenyl phosphate (NDPP) is another reagent for the active ester-type mixed anhydride method.

D. Carbodiimide Methods: When using carbodiimide, an activated intermediate, which is produced by reaction of a protected amino acid and the carbodiimide, undergoes aminolysis. The reaction of an N-protected amino acid and carbodiimide without an amine component gives another activated species, which also reacts with amine components. Water-soluble carbodiimides such as 1-ethyl-3-(3'-dimethylaminopropyl)carbodiimide have been developed, in such systems, both the reagent and the resulting urea derivative are soluble and easily removable by washing.

E. DCC-Additive Methods: Fragment condensation using DCC and HOSu under strictly controlled conditions preserves the chiral purity almost completely.

F. Azide Methods: The hydrazide is prepared by treating and N-protected amino acid or peptide ester with excess hydrazine hydrate. The hydrazide is converted to azide by tert-butyl or isoamyl nitrite, and the azide reacts with the amine component without extraction with organic solvent.

G. Protected Hydrazide Methods: Peptide esters containing Arg(NO2), Asp(O-t-Bu), Asp(Obzl) (where t-Bu and Bzl represents tert-butyl and benzyl, respectively) cannot be converted to the corresponding hydrazide by hydrazinolysis. In such cases, a protected hydrazide is introduced at the C-terminus of a peptide or carboxyl group of an amino acid. After elongation of the peptide chain, the substituent on the hydrazide is removed, and the resulting hydrazide is converted to an azide. Various protected hydrazides are known in the art. The usual protecting groups for hydrazine are 2,tert-butoxycarbonyl, 2,2,2-trichloroethyloxycarbonyl, and 2,2,2-trichloro-tert-butoxycarbonyl.

(i) Azide Method Using Dephenylphosphorylazide: A free carboxyl group is directly converted to an azide by diphenylphosphorylazice (DPPA). The coupling reaction is considered to proceed via an azide rather than an acyloxyphosphoric mixed anhydride, which is also a likely intermediate. One of skill in the art will recognize that similar reagents such as diethylphosphorocyanidate (DEPC) can be used.

H. Phosphonium and Uronium Salt Type Coupling Reagents: benzotriazole-1-yloyxtris(dimethylamino) phosphonium hexafluorophosphate (bop) is an excellent coupling reagent offering high reactivity and easy handling. The reaction between bop and N-protected amino acid proceeds via an acyloxyphosphonium as an intermediate to produce the corresponding bonzotriazole ester and easily removable by-products such as hexamethylphosphoric triamide (hmpa) and salts. However, hmpa, the starting material in the synthesis and a by-product in the reaction of bop, have been reported to have respiratory toxicity. It is therefore contemplated that bop can be replaced by benzotriazole-1-yloxytrspyrrolidinophosphonium hexafluorophosphate (pybop), which has similar reactivity to bop but forms no carcinogenic by-products.

2-(1H-Benzotriazole-1-yl)-oxy-1,3,3-tetramethyluronium hexafluorophosphate (HBTU), 2-[2-oxo-1(2H)-pyridyl)-1,1,3,3-bispentamethyleneuronium tetrafluoroborate (TOPPipU), and 2-(benzotriazole-1-yl)-oxy-1,3 -dimethylimidazolidinium hexafluorophosphate have similar reactivities to BOP. Phosphonium is substituted by uronium in these reagents. 1-hydroxy-7-azabenzotriazole (HOAt), and additive, and 2-(1H-7-azabenzotriazole-1-yl)-oxy-1,1,3,3-tetramethyluronium hexafluorophosphate (HATU), a uronium-type coupling reagent containing the HOAt moiety, enhance the coupling reaction rate and reduce the loss of chiral integrity.

Bromotrispyrrolidinophosphonium hexafluorophosphate (PyBroP) and 2-chloro-1,3-dimethylimidazolidinium hexafluorophosphate have been developed as coupling reagents for N-methylamino acids or α-dealkylamino acids and as esterification reagents.

Group Additions and Deletions

A variation to the method of thioretinamide synthesis could be made, by the addition or temporary deletion of chemical groups (such as methyl groups) or addition or temporary deletion of double bonds in order to protect the molecule during reaction as will be apparent to one of ordinary skill in the art.

Cis/Trans Isomers

Instead of starting with all-trans-retinoic-acid, one of ordinary skill in the art will recognize that one may start with various cis-forms of retinoic acid and have successful synthesis of thioretinamide.

Racemization

The synthesis to include any racemic mixture of homocysteine thiolactone and retinoic acid and any thioretinamide conformation.

Solvents of Reaction

Thioretinamide is soluble in non-polar/organic solvents. A variety of non-polar/organic solvents, generally known to one of ordinary skill in the art, could be used in the synthesis and purification of thioretinamide.

Duration of Reaction

The duration of reactions/procedures listed in the synthesis of thioretinamide in Example 2 are not absolute, but are merely guidelines. A person of skill in the art will appreciate that it is possible to produce thioretinamide in a shorter period of time, or in a longer period of time, than listed in the synthesis method in Example 2. The yield may vary accordingly.

Temperature of Reactions

The temperature of the various stages of synthesis described in Example 2 is not to be regarded as an absolute for successful synthesis of thioretinamide. The skilled artisan will recognize that it is possible to produce thioretinamide at higher and lower temperatures during different steps of the synthesis.

Pressure Conditions of Reaction

The different pressure conditions are not considered as variations in the production of thioretinamide. Reduced pressure was often used to hasten evaporation of solvents, and is not critical to successful synthesis of thioretinamide.

Light Conditions

One of skill in the art will realize that thioretinamide can be synthesized under light conditions that differ from those described in Example 2. Therefore, synthesis should not be considered altered if performed under various light conditions.

Anhydrous Conditions

Thioretinamide synthesis should not be considered altered if performed under various hydrated conditions and this will be appreciated by the skilled artisan.

Separation/Purification Method

Thioretinamide synthesis should not be considered altered if various separation/purification methods are used include among others methods such as, thin layer chromatography, high performance liquid chromatography, aqueous/organic solvent washes, flash chromatography, centrifugal chromatography and recrystalization in various organic solvents known to one of ordinary skill in the art.

EXAMPLE 4

Analysis of N-Homocysteine Thiolactonyl Retinamide

Figure 6:
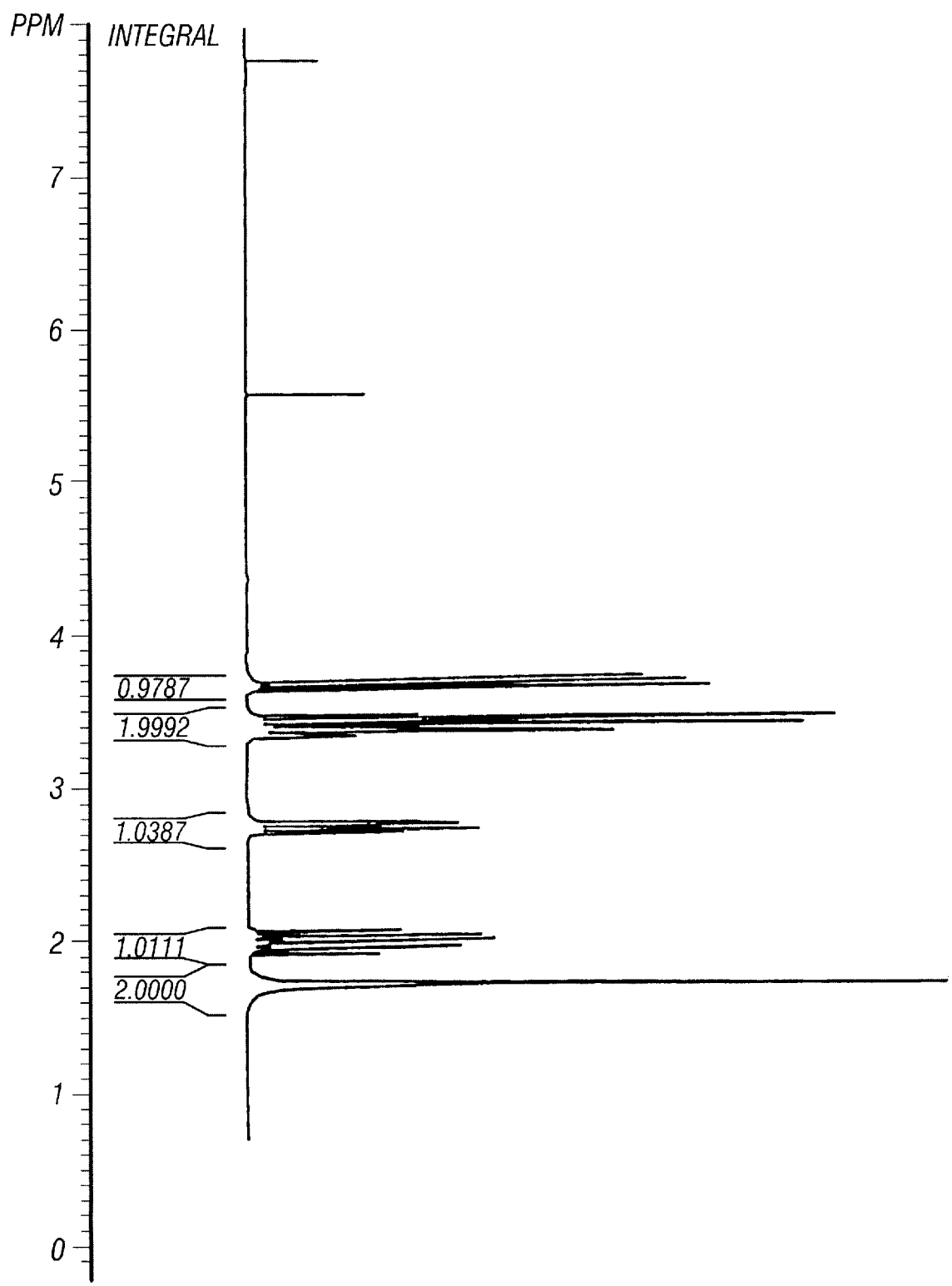
FIG. 6. Proton N.M.R. of homocysteine thiolactone made according to the invention. 300 mHz proton N.M.R. of homocysteine thiolactone performed in the solvent chloroform.
Figure 7:
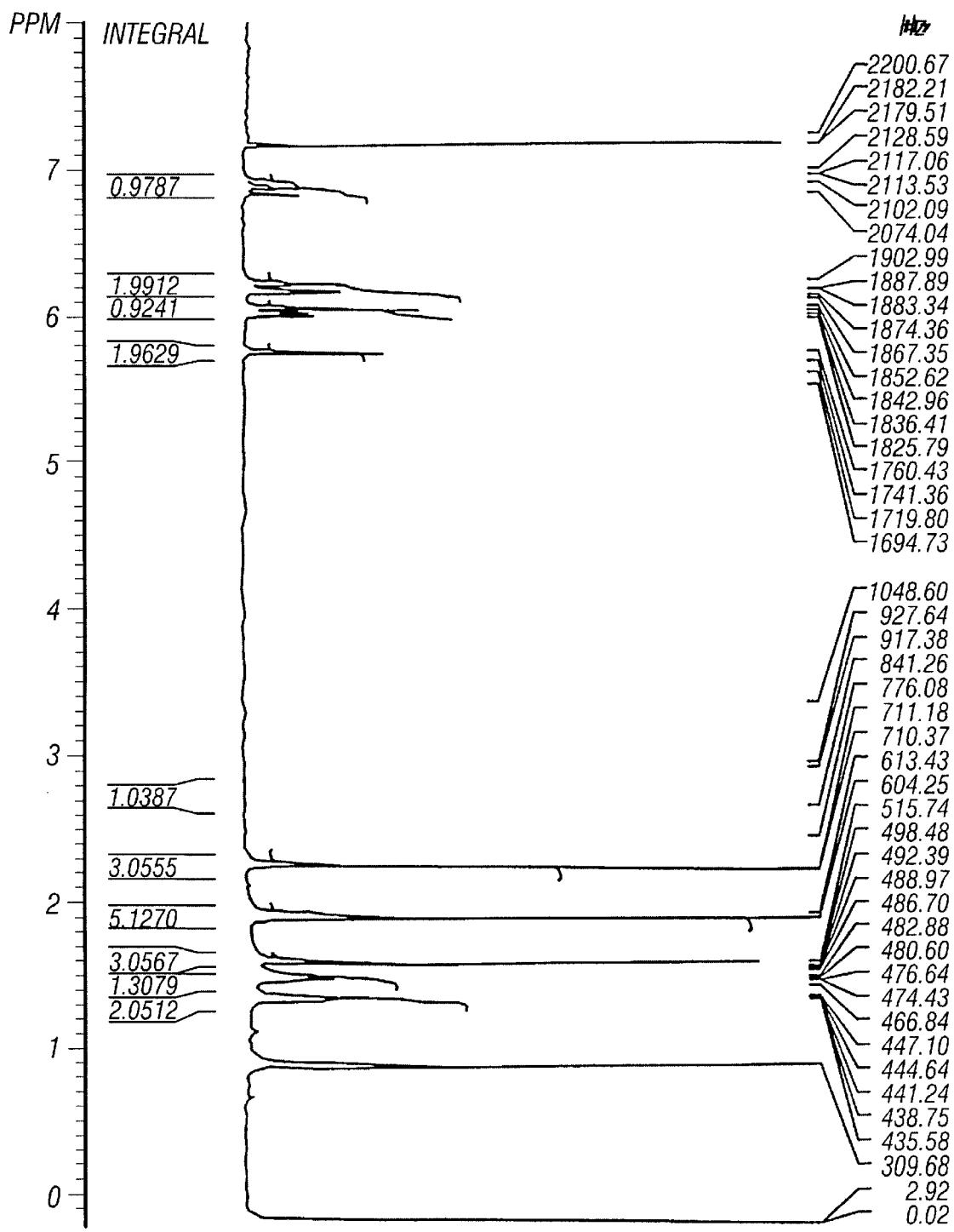
FIG. 7. Proton N.M.R. of retinoic acid. 300 mHz proton N.M.R. of retinoic acid performed in the solvent chloroform.

Verification of thioretinamide synthesis was performed by using proton and carbon N.M.R. and mass spectroscopy. The proton N.M.R. of thioretinamide (FIG. 5) shows both homocysteine thiolactone (FIG. 6) and retinoic acid (FIG. 7) as constituents of thioretinamide. The proton N.M.R. of thioretinamide (FIG. 5) at 1.0–2.4 ppm consists of singlet peaks integrating for the three methyl group hydrogens of the retinoic acid component of thioretinamide. Peaks at 2.9–4.6 ppm correspond to the protons of the homocysteine thiolactone ring of thioretinamide. The peaks at 5.7–7.0 ppm represent the unsaturated protons, vinyl protons, of the retinoic acid component of thioretinamide. The conjugation of homocysteine thiolactone and retinoic acid at the homocysteine thiolaconyl amide is indicated by downfield shifting of proton signals of the amide hydrogen thioretinamide N.M.R. The synthesis of thioretinamide reported by McCully and Vezeridis (1987a) using 60 mHz N.M.R., which reported multiplets 1.1–2.2, triplet 6.3, and singlet 7.2 ppm, does not confirm that thioretinamide was successfully synthesized.

Figure 8:
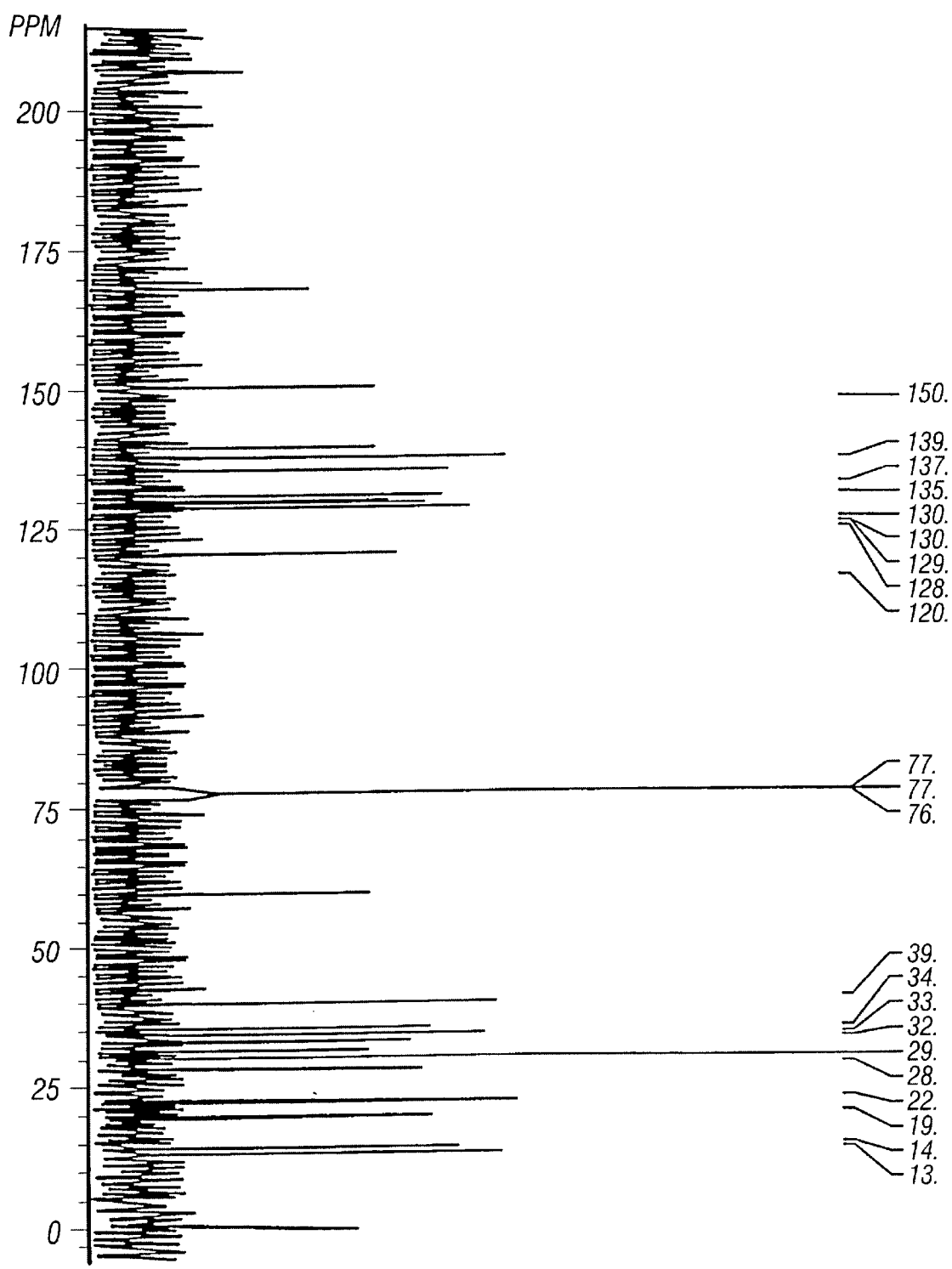
FIG. 8. Carbon N.M.R. of homocysteine thiolactonyl retinamide made according to the invention.

The carbon N.M.R. of thioretinamide (FIG. 8) provided further evidence that thioretinamide was in fact the compound that had been produced. The number of carbon atoms shown by the carbon N.M.R. (27) corresponded to the number of carbon atoms in thioretinamide (24) plus the number of carbon atoms found in the solvent chloroform (3). Identification of carbon atom peaks include the following: Five methyl group carbons are located at 0–30 ppm. Three carbons from the benzene ring and one carbon from the homocysteine thiolactone ring are represented by the four peaks at 30–40 ppm. The non-carboxyl carbon atom located next to the sulfur atom is represented by the peak at 60 ppm. Ten carbon atoms located in the conjugated double bonds of thioretinamide are represented by the peaks at 120–150 ppm. The carboxyl carbon atom of the homocysteine thiolactone ring is represented by the peak at 167 ppm and the carboxyl carbon atom of the retinoic acid back-bone is represented by the peak at 205 ppm. The three peaks at 75–80 ppm represent carbon atoms of the solvent chloroform. Mass spectroscopy results showed that thioretinamide, designated by chemical formula $C_{24}H_{33}NO_2S$ (Table 1 and FIG. 9), had the molecular mass of 399.22320.

The melting point of thioretinamide was determined to be about 156–158° C. This differs from the melting point of 172–173° C. reported by McCully and Vezeridis (1987a).

TABLE 1

Mass Spectroscopy of Thioretinamide
Elemental Composition
File: JAN21ETA Ident: 89 Acq: 21-JAN-1999 16.44:51 Cal: JAN21ETA
ProSpecE EI+ Magnet BpM: 69 BpI: 1906176 TIC: 16734541 Flags: ACC
Sample Text: SW1 File Text: M. Kazimir, C24H32NS02, 398.21538
Heteroatom Max: 20    Ion: Both Even and Odd Limits:

| | | | | | | | | | | | |
|---|---|---|---|---|---|---|---|---|---|---|---|
| 390.983 | 1.0 | | | | | | -0.5 | 0 | 0 | 0 | 0 | 0 |
| 410.965 | 100.0 | | | | 10.0 | | 30.0 | 50 | 50 | 5 | 10 | 5 |

| Mass | %RA | Pks | Std | PPM | mDa | Calc. Mass | DBE | C | H | N | O | S |
|---|---|---|---|---|---|---|---|---|---|---|---|---|
| 401.225159 | 5.5 | | | -19.0 | -7.6 | 401.217543 | 4.5 | 20 | 33 | | 8 | |
| | | | | 19.0 | 7.6 | 401.232800 | 8.5 | 24 | 33 | | 5 | |
| | | | | -20.2 | -8.1 | 401.217071 | 4.0 | 19 | 35 | 3 | 2 | 2 |
| | | | | 21.2 | 8.5 | 401.233.670 | 7.5 | 25 | 37 | | | 2 |
| | | | | -22.3 | -9.0 | 401.216201 | 5.0 | 18 | 31 | 3 | 7 | |
| | | | | 22.4 | 9.0 | 401.234137 | 13.5 | 25 | 29 | 4 | 1 | |
| | | | | 24.1 | 9.7 | 401.234829 | 4.0 | 19 | 35 | 3 | 4 | 1 |
| 400.225822 | 19.2 | | | 0.1 | 0.0 | 400.225845 | 8.0 | 25 | 36 | | | 2 |
| | | | | 1.2 | 0.5 | 400.226312 | 14.0 | 25 | 28 | 4 | 1 | |
| | | | | -2.1 | -0.8 | 400.224974 | 9.0 | 24 | 32 | | 5 | |
| | | | | 3.0 | 1.2 | 400.227004 | 4.5 | 19 | 34 | 3 | 4 | 1 |
| | | | | -3.7 | -1.5 | 400.224324 | 0.0 | 16 | 36 | 2 | 7 | 1 |
| | | | | 4.6 | 1.8 | 400.227654 | 13.5 | 27 | 30 | 1 | 2 | |
| | | | | -4.9 | -2.0 | 400.223852 | -0.5 | 15 | 38 | 5 | 1 | 3 |
| | | | | -5.5 | -2.2 | 400.223632 | 9.5 | 22 | 30 | 3 | 4 | |
| | | | | 6.3 | 2.5 | 400.228346 | 4.0 | 21 | 36 | | 5 | 1 |
| | | | | -7.1 | -2.8 | 400.222981 | 0.5 | 14 | 34 | 5 | 6 | 1 |
| | | | | -8.4 | -3.3 | 400.222473 | 13.0 | 28 | 32 | | | 1 |
| | | | | 8.5 | 3.4 | 400.229217 | 3.0 | 22 | 40 | | | 3 |
| | | | | 9.2 | 3.7 | 400.229505 | 0.5 | 15 | 34 | 3 | 9 | |
| | | | | 9.6 | 3.9 | 400.229684 | 9.0 | 22 | 32 | 4 | 1 | 1 |
| | | | | -10.0 | -4.0 | 400.221822 | 4.0 | 20 | 36 | 2 | 2 | 2 |
| | | | | 11.4 | 4.6 | 400.230376 | -0.5 | 16 | 38 | 3 | 4 | 2 |
| | | | | -12.2 | -4.9 | 400.220952 | 5.0 | 19 | 32 | 2 | 7 | |
| | | | | 12.6 | 5.0 | 400.230848 | 0.0 | 17 | 36 | | 10 | |
| | | | | 13.0 | 5.2 | 400.231026 | 8.5 | 24 | 34 | 1 | 2 | 1 |
| | | | | -13.3 | -5.3 | 400.220480 | 4.5 | 18 | 34 | 5 | 1 | 2 |
| | | | | -15.5 | -6.2 | 400.219609 | 5.5 | 17 | 30 | 5 | 6 | |
| | | | | 15.9 | 6.4 | 400.232185 | 5.0 | 18 | 32 | 4 | 6 | |
| | | | | -16.7 | -6.7 | 400.219142 | -0.5 | 17 | 38 | 1 | 5 | 2 |
| | | | | -16.8 | -6.7 | 400.219101 | 18.0 | 31 | 28 | | | |
| | | | | 18.1 | 7.2 | 400.233056 | 4.0 | 19 | 36 | 4 | 1 | 2 |
| | | | | -18.4 | -7.4 | 400.218450 | 9.0 | 23 | 32 | 2 | 2 | 1 |
| | | | | -18.9 | -7.6 | 400.218272 | 0.5 | 16 | 34 | 1 | 10 | |
| | | | | 19.3 | 7.7 | 400.233528 | 4.5 | 20 | 34 | 1 | 7 | |
| | | | | -20.0 | -8.0 | 400.217800 | 0.0 | 15 | 36 | 4 | 4 | 2 |
| | | | | 21.4 | 8.6 | 400.234398 | 3.5 | 21 | 38 | 1 | 2 | 2 |
| | | | | -21.8 | -8.7 | 400.217108 | 9.5 | 21 | 30 | 5 | 1 | 1 |
| | | | | -22.2 | -8.9 | 400.216929 | 1.0 | 14 | 32 | 4 | 9 | |
| | | | | 22.6 | 9.0 | 400.234865 | 9.5 | 21 | 30 | 5 | 3 | |
| | | | | -22.9 | -9.2 | 400.216641 | 3.5 | 21 | 38 | 1 | | 3 |
| | | | | 24.3 | 9.7 | 400.235557 | 0.0 | 15 | 36 | 4 | 6 | 1 |
| 399.222427 | 70.9 | | | 0.3 | 0.1 | 399.222551 | 0.0 | 16 | 37 | 3 | 4 | 2 |
| | | | | -1.4 | -0.6 | 399.221859 | 9.5 | 22 | 31 | 4 | 1 | 1 |
| | | | | 1.5 | 0.6 | 399.223023 | 0.5 | 17 | 35 | | 10 | |
| | | | | -1.9 | -0.7 | 399.221680 | 1.0 | 15 | 33 | 3 | 9 | |
| | | | | 1.9 | 0.8 | 399.223201 | 9.0 | 24 | 33 | 1 | 2 | 1 |
| | | | | -2.6 | -1.0 | 399.221392 | 3.5 | 22 | 39 | | | 3 |

A positive ion, accurate mass analysis calculated the mass of thioretinamide ($C_{24}H_{33}NO_2S$) to be 399.223201. Chemical formula and calculated mass is designated by box in Table 1.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods disclosed and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

McCully, K. S., Olszewski, A. J., Vezeridis, M. P., Homocysteine and lipid metabolism in atherogenesis: effect of the homocysteine thiolactonyl derivatives, thioretinaco and thioretinamide, *Atherosclerosis*, 83:197–206, 1990.

McCully, K. S., Homocysteine thiolactone metabolism in malignant cells, *Cancer Research*, 36: 3198–3202; 1976.

McCully, K. S. and Clopath, P., Homocysteine compounds which influence the growth of a malignant neoplasm, *Chemotherapy*, 23: 44–49; 1997.

McCully, K. S. and Vezeridis, M. P., Antineoplastic activity of a rhodium trichloride complex of oxalyl homocysteine thiolactone, *Cancer Investigation*, 5: 25–30; 1987b.

McCully, K. S. and Vezeridis, M. P., Antineoplastic activity of N-maleamide homocysteine thiolactone amide encapsulated within liposomes, *Proceedings of the Society of Experimental Biology and Medicine*, 180: 57–61; 1985.

McCully, K. S. and Vezeridis, M. P., Chemopreventive and antineoplastic activity of N-homocysteine thiolactonyl retinamide, *Carcinogenesis*, 8: 1559–1562; 1987a.

McCully, K. S. and Vezeridis, M. P., Chemopreventive effect of N-homocysteine thiolactonyl retinamido cobalamin on carcinogenesis by ethyl carbamate in mice, *Proceedings of the Societyfor Experimental Biology and Medicine*, 191: 346–351; 1989.

McCully, K. S., Tzanakakis, G. N., and Bezeridis, M. P., Inhibition of neoplastic growth by N-homocysteine thiolactonyl retinamido cobalamin, *Research Communications in Chemical Pathology and Pharmacology*, 66: 117–122; 1989.

McCully, K. S., Tzanakakis, G. N., and Vezeridis, M. P., Effect of the homocysteine thiolactonyl derivatives, thioretinaco, thioretinamide and thioco on growth and lactate production by malignant cells, *Research Communications in Chemical Pathology and Pharmacology*, 77: 125–128; 1992.

Moon, R. C. and Itri, L. M., Retinoids and cancer, In: Sporn, M. B., Roberts, A. B., Goodman, D. S. (eds), The retinoids, Academic Press, Orlando, Fla., 2: 327–371; 1984.

"Peptides: synthesis, structures, and applications," edited by Bemd Butte, Copyright© 1995 by Academic Press, Inc., San Diego, Calif., pp 40–53.

Spindel and McCully, *Biochimica et Biophysica Acta*, 343:687–691, 1974.

Sundaresen, P. R., Vitamin A and the sulfate-activating enzymes, *Biochimica et Biophysica Acta*, 113: 95–109; 1966.

U.S. Pat. No. 4,255,443
U.S. Pat. No. 4,383,994
U.S. Pat. No. 4,618,685
U.S. Pat. No. 4,925,931

What is claimed is:

1. A method for the synthesis of N-homocysteine thiolactonyl retinamido cobalamin, said method comprising:

a) conjugating, in a single reaction mixture, retinoic acid with a homocysteine thiolactone using at least a first coupling agent to obtain N-homocysteine thiolactonyl retinamide; and b) admixing 5'-deoxyadenosine cobalamin with the N-homocysteine thiolactonyl retinamide to produce N-homocysteine thiolactonyl retinamido cobalamin.

2. The method of claim 1, wherein the N-homocysteine thiolactonyl retinamide is racemic DL-N-homocysteine thiolactonyl retinamide.

3. The method of claim 1, wherein the N-homocysteine thiolactonyl retinamide is L-N-homocysteine thiolactonyl retinamide.

4. The method of claim 1, wherein the N-homocysteine thiolactonyl retinamide is D-N-homocysteine thiolactonyl retinamide.

5. The method of claim 1, wherein the 5'-deoxyadenosine cobalamin is any isomeric variant.

6. The method of claim 1, further comprising adding a conjugating agent to the mixture of 5'-deoxyadenosine cobalamin and N-homocysteine thiolactonyl retinamide.

7. The method of claim 1, wherein the reaction is performed under conditions of reduced light.

8. The method of claim 1, wherein the reaction is performed under an atmosphere of argon.

9. The method of claim 1, further comprising analysis of the product by nuclear magnetic resonance spectroscopy.

10. The method of claim 1, further comprising analysis of the product by mass spectroscopy.

11. The method of claim 1, further comprising analysis of the product by x-ray crystallography.

12. The method of claim 1, further comprising dissolving the N-homocysteine thiolactonyl retinamide in a solvent prior to adding 5'-deoxyadenosine cobalamin.

13. The method of claim 12, wherein the solvent used to dissolve N-homocysteine thiolactonyl retinamide is ethanol.

14. The method of claim 13, further comprising evaporating the ethanol under reduced pressure.

15. The method of claim 12, wherein the solvent used to dissolve the N-homocysteine thiolactonyl retinamide is hydrochloric acid.

16. The method of claim 1, wherein the first coupling agent is N-ethyl N'-(3-dimethyl-aminopropyl) carboduimide.

17. The method of claim 1, further comprising the use of a second coupling agent.

18. The method of claim 17, wherein the second coupling agent is 1-hydroxybenzotriazole.

19. The method of claim 17, wherein the second coupling agent is 3-hydroxy-4-oxo-3,4-dihydro-1,2,3-benzotriazine.

20. The method of claim 1, wherein the second coupling agent is benzotriazole-1-yloxytris(dimethylamino)phosphonium hexafluorophosphate.

21. The method of claim 1, wherein the retinoic acid is dissolved in a solvent prior to the addition of the homocysteine thiolactone.

22. The method of claim 19, wherein the solvent used to dissolve retinoic acid is N,N-dimethylformamide.

23. The method of claim 19, wherein the solvent used to dissolve retinoic acid is ethyl acetate.

24. The method of claim 1, wherein N-homocysteine thiolactonyl retinamido cobalamin of 70% or greater purity is produced.

25. A method for the synthesis of substantially pure N-homocysteine thiolactonyl retinamide cobalamin comprising conjugating N-homocysteine thiolactonyl retinamide with 5'-deoxyadenosine cobalamin.

* * * * *

UNITED STATES PATENT AND TRADEMARK OFFICE
CERTIFICATE OF CORRECTION

PATENT NO. : 6,287,818 B1
DATED : September 11, 2001
INVENTOR(S) : Kazimir et al.

It is certified that error appears in the above-identified patent and that said Letters Patent is hereby corrected as shown below:

Column 16,
Lines 61 and 62, please delete "carboduimide" and insert -- carbodiimide -- therefor.

Signed and Sealed this

Fourth Day of June, 2002

Attest:

Attesting Officer

JAMES E. ROGAN
Director of the United States Patent and Trademark Office